(12) United States Patent
Manetsch et al.

(10) Patent No.: US 10,081,607 B2
(45) Date of Patent: Sep. 25, 2018

(54) COMPOSITIONS, METHODS OF USE, AND METHODS OF TREATMENT

(71) Applicants: Roman Manetsch, Tampa, FL (US); Lindsey Neil Shaw, Tampa, FL (US); Kurt Steven Van Horn, Tampa, FL (US); Whittney Nicole Burda, Tampa, FL (US)

(72) Inventors: Roman Manetsch, Tampa, FL (US); Lindsey Neil Shaw, Tampa, FL (US); Kurt Steven Van Horn, Tampa, FL (US); Whittney Nicole Burda, Tampa, FL (US)

(73) Assignee: University of South Florida, Tampa, FL (US)

( * ) Notice: Subject to any disclaimer, the term of this patent is extended or adjusted under 35 U.S.C. 154(b) by 108 days.

(21) Appl. No.: 14/529,507

(22) Filed: Oct. 31, 2014

(65) Prior Publication Data
US 2015/0080409 A1   Mar. 19, 2015

Related U.S. Application Data

(63) Continuation of application No. 13/848,846, filed on Mar. 22, 2013, now Pat. No. 8,906,918.

(60) Provisional application No. 61/614,849, filed on Mar. 23, 2012.

(51) Int. Cl.
| | |
|---|---|
| *A61K 31/517* | (2006.01) |
| *C07D 239/95* | (2006.01) |
| *A01N 43/54* | (2006.01) |
| *C07D 401/12* | (2006.01) |
| *C07D 405/12* | (2006.01) |
| *C07D 405/14* | (2006.01) |
| *A01N 43/60* | (2006.01) |
| *A01N 43/90* | (2006.01) |

(52) U.S. Cl.
CPC .......... *C07D 239/95* (2013.01); *A01N 43/54* (2013.01); *A01N 43/60* (2013.01); *A01N 43/90* (2013.01); *A61K 31/517* (2013.01); *C07D 401/12* (2013.01); *C07D 405/12* (2013.01); *C07D 405/14* (2013.01)

(58) Field of Classification Search
CPC .................................................. A61K 31/517
USPC ...................................................... 514/266.4
See application file for complete search history.

(56) References Cited

U.S. PATENT DOCUMENTS 8,933,096 B2 * 1/2015 Lavoie ................. C07D 217/14
514/307

OTHER PUBLICATIONS

Font, M. et al., European Journal of Medicinal Chemistry, 46 (2011), pp. 3887-3899.*
Frontiers Research Topics—The Staphylococci and Staphylococcal Pathogenesis, David Heinrichs and Martin J. McGavin, copyright 2007-2012.*

(Continued)

*Primary Examiner* — Shengjun Wang
(74) *Attorney, Agent, or Firm* — Thomas | Horstemeyer, LLP

(57) ABSTRACT

Embodiments of the present disclosure, in one aspect, relate to a 2,4-diaminoquinazoline compound, pharmaceutical compositions including a 2,4-diaminoquinazoline compound, methods of treatment of a condition (e.g., infection) or disease, methods of treatment using compositions or pharmaceutical compositions, and the like.

15 Claims, 24 Drawing Sheets

Structure A

(56) References Cited

OTHER PUBLICATIONS

Gangjee, et al., Current Pharmaceutical Design, 2007, 13, pp. 609-639.*

Nanda, A. K., Ganguli, S., & Chakraborty, R. (2007). Antibacterial activity of some 3-(Arylideneamino)-2-phenylquinazoline-4 (3H)-ones: synthesis and preliminary QSAR studies. Molecules, 12(10), 2413-2426.

Antipenko, L. N., Karpenko, A. V., Kovalenko, S. I., Katsev, A. M., Komarovska-Porokhnyavets, E. Z., & Novikov, V. P. (2009). Synthesis, Cytotoxicity by Bioluminescence Inhibition, Antibacterial and Antifungal Activity of ([1, 2, 4] Triazolo [1, 5-c] quinazolin-2-ylthio) carboxylic Acid Amides. Archiv der Pharmazie, 342(11), 651-662.

Rohini, R., Muralidhar Reddy, P., Shanker, K., Hu, A., & Ravinder, V. (2010). Antimicrobial study of newly synthesized 6-substituted indolo [1, 2-c] quinazolines. European journal of medicinal chemistry, 45(3), 1200-1205.

Huband, M. D., Cohen, M. A., Zurack, M., Hanna, D. L., Skerlos, L. A., Sulavik, M. C., Gibson, G. W., Gage, J. W., Ellsworth, E., Stier, M. A., Gracheck, S. J. (2007) In vitro and in vivo activities of PD 0305970 and PD 0326448, new bacterial gyrase/topoisomerase inhibitors with potent antibacterial activities versus multidrug-resistant gram-positive and fastidious organism groups. Antimicrobial agents and chemotherapy, 51(4), 1191-1201.

\* cited by examiner

Structure A

Structure A

FIG 6.A, TABLE 1.A

| Compound Name | Structure | Staphylococcus aureus MIC | Acinetobacter baumannii MIC | E. faecalis MIC | B. anthracis MIC |
|---|---|---|---|---|---|
| KVH1.46 | 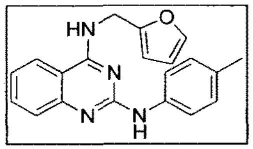 | 5-10 | ND | | |
| KVH1.147 | 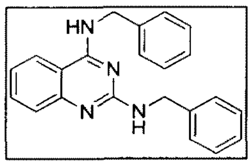 | <1 | ND | | <1 |
| KVH1.149 | 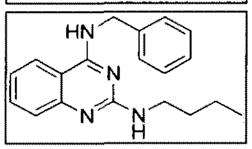 | <1 | >25 | | <1 |
| KVH1.150 | 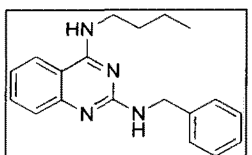 | ND | >100 | | |
| KVH1.151 | 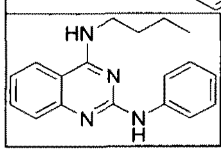 | 5-10 | >25 | | |

FIG. 6.B, TABLE 1.B

| | | | | | |
|---|---|---|---|---|---|
| | >25 | ND | >25 | >25 | >100 |
| | 1-10 | 5-10 | 5-10 | 5-10 | ND |
| | KVH1.152 | KVH1.153 | KVH1.154 | KVH1.155 | KVH1.168 |

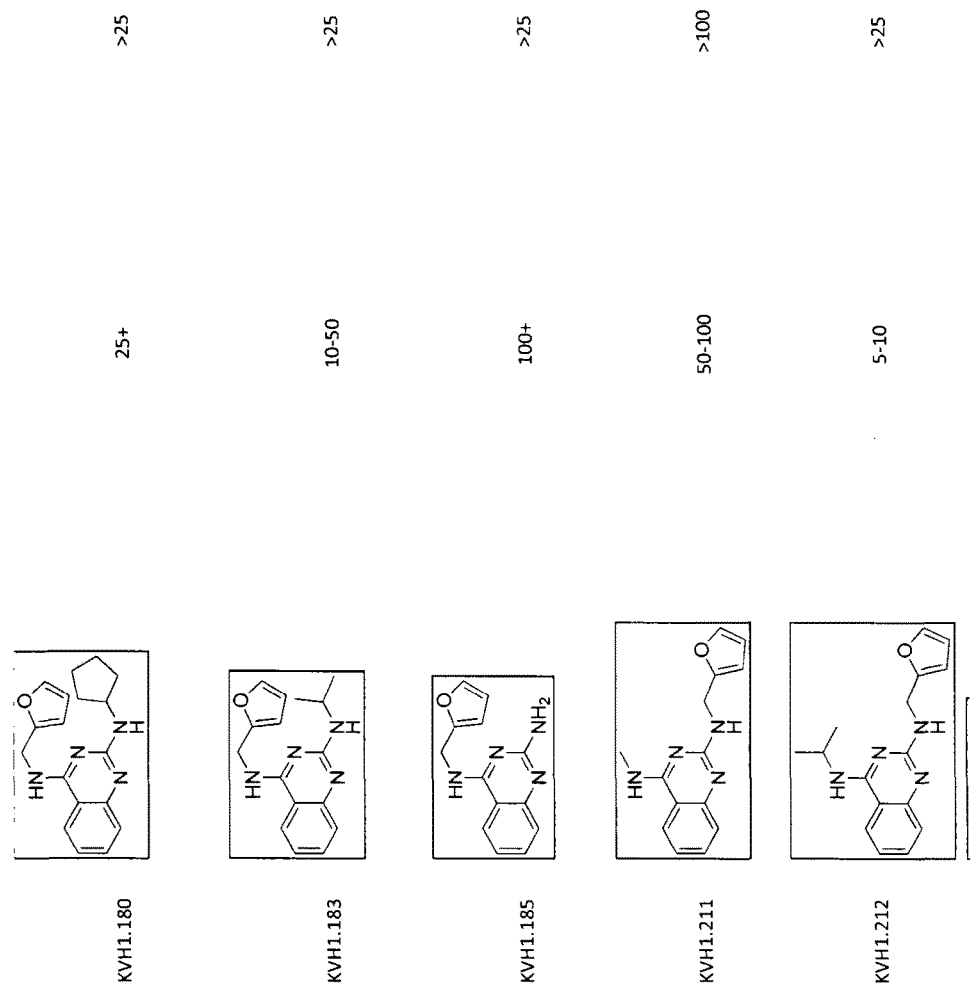
FIG 6.C, TABLE 1.C

FIG 6.D, TABLE 1.D
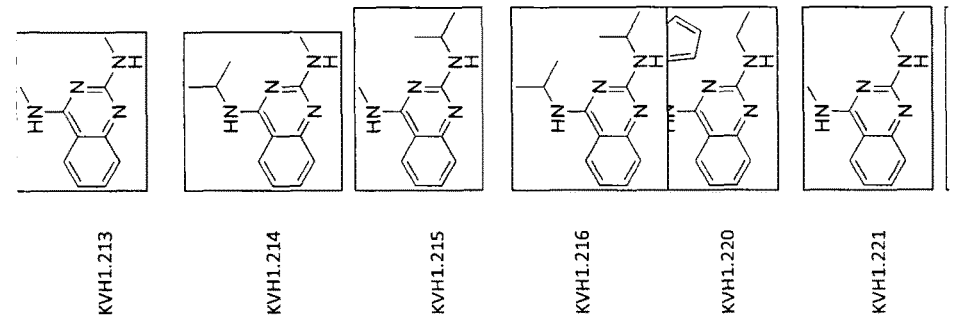
| KVH1.213 | KVH1.214 | KVH1.215 | KVH1.216 | KVH1.220 | KVH1.221 |
|---|---|---|---|---|---|
| >25 | >25 | >25 | >25 | >25 | >25 |
| >25 | >25 | >25 | >25 | >25 | >25 |

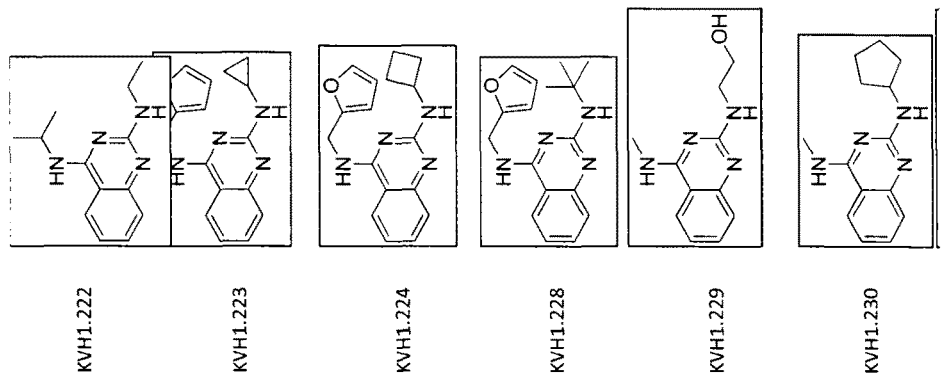
FIG 6.E, TABLE 1.E

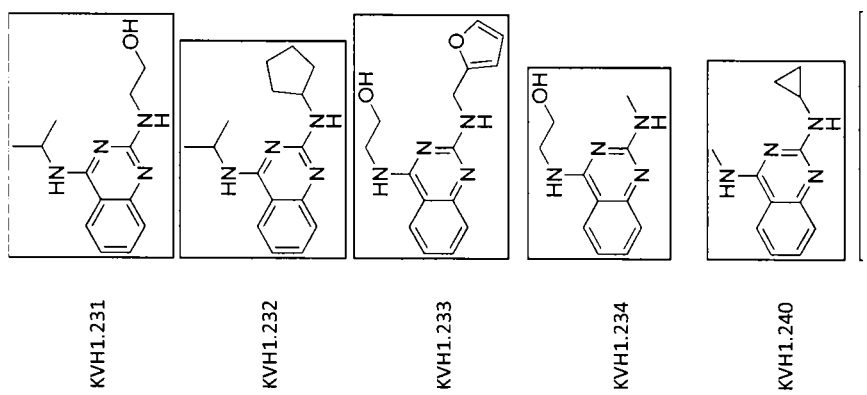
FIG 6.F, TABLE 1.F
| | KVH1.231 | KVH1.232 | KVH1.233 | KVH1.234 | KVH1.240 |
|---|---|---|---|---|---|
| | >25 | >25 | >25 | >25 | >25 |
| | >25 | 10-50 | >25 | >25 | 50-100 |

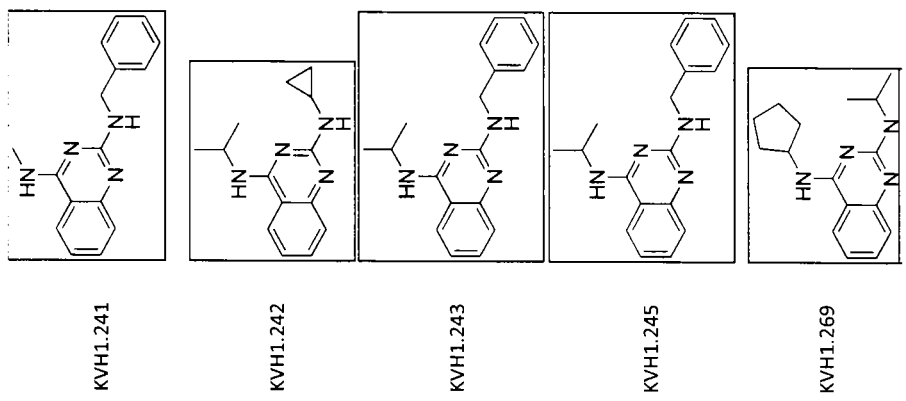
FIG 6.G, TABLE 1.G
| Compound | Value 1 | Value 2 |
|---|---|---|
| KVH1.241 | ND | >25 |
| KVH1.242 | >25 | >25 |
| KVH1.243 | 5-10 | 50 |
| KVH1.245 | >25 | >25 |
| KVH1.269 | 5-10 | >25 |

FIG 6.H, TABLE 1.H
| | | | | |
|---|---|---|---|---|
| >25 | >25 | >25 | >25 | >25 |
| >25 | 100+ | >25 | 5-10 | 5-10 |
| 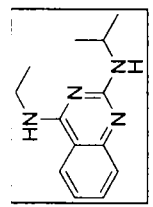 | 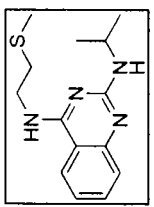 | 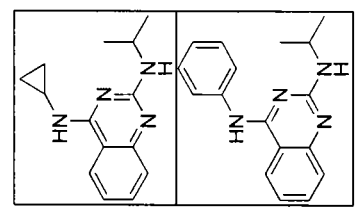 | | 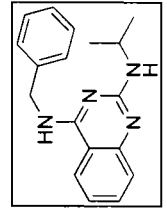 |
| KVH1.270 | KVH1.271 | KVH1.272 | KVH1.273 | KVH1.274 |

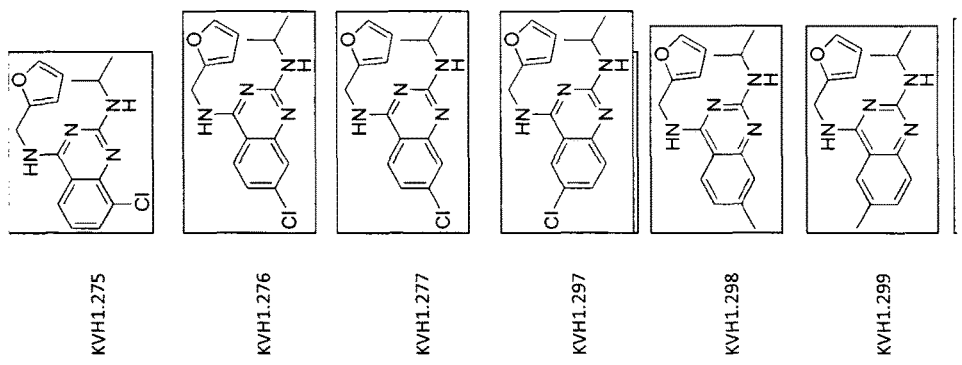
FIG 6.I, TABLE 1.I

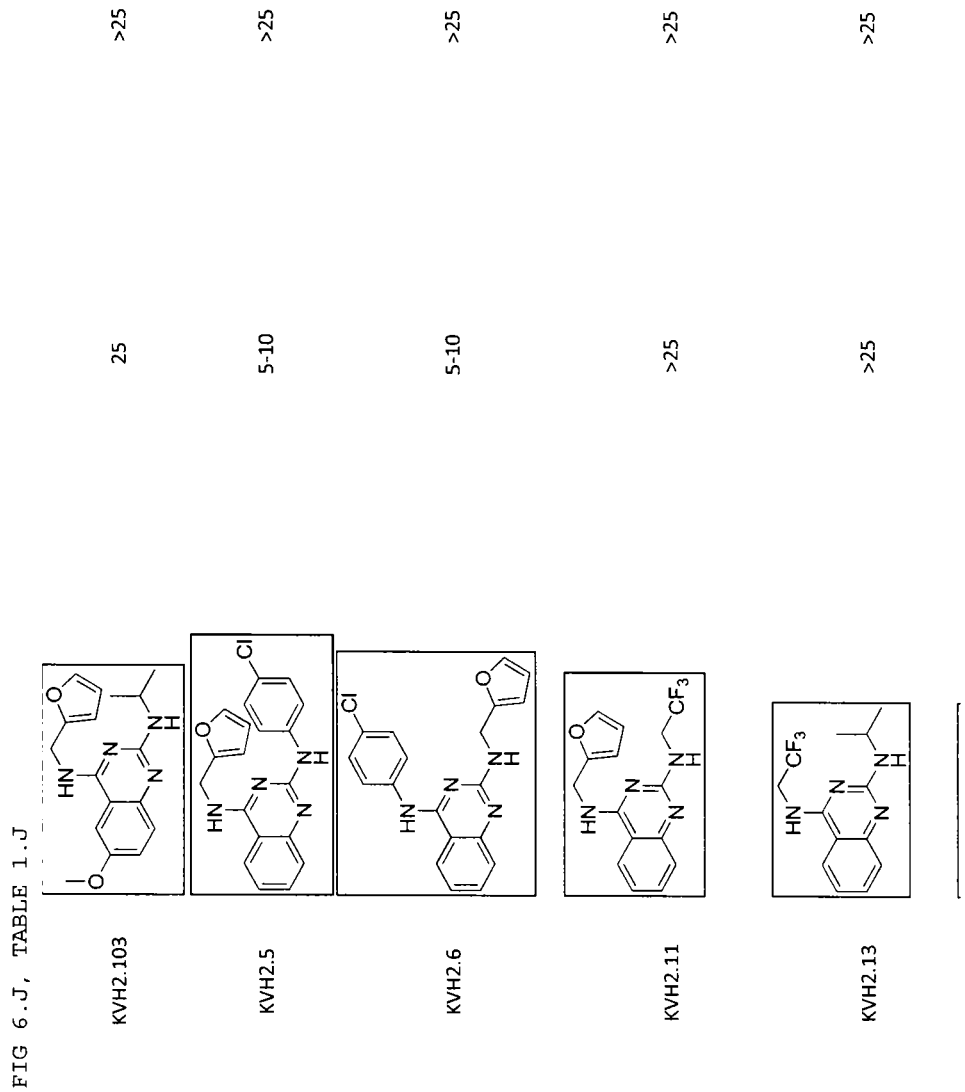

FIG 6.K, TABLE 1.K
| | | | |
|---|---|---|---|
| >25 | >25 | >25 | >25 |
| >25 | >25 | >25 | >25 |
| 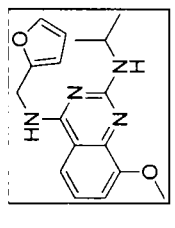 | 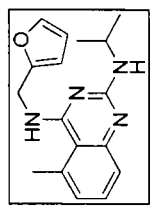 | 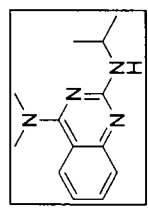 | 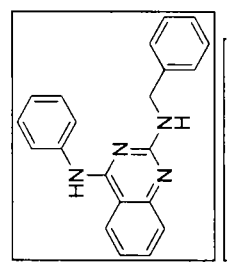 |
| KVH2.18 | KVH2.52 | KVH2.54 | KVH2.56 |

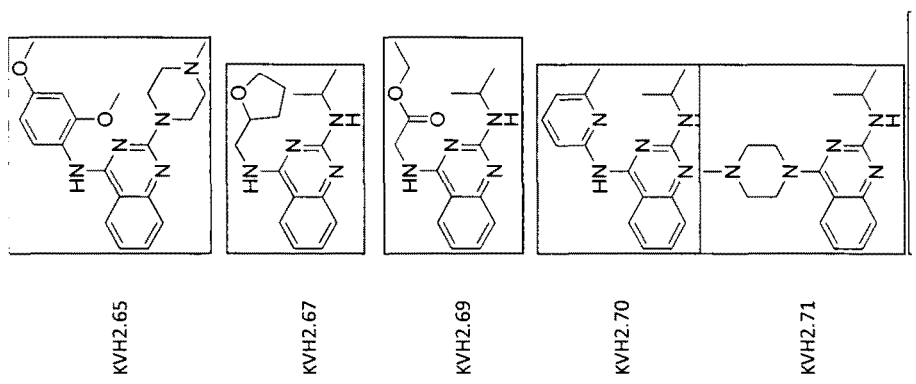
FIG 6.L, TABLE 1.L

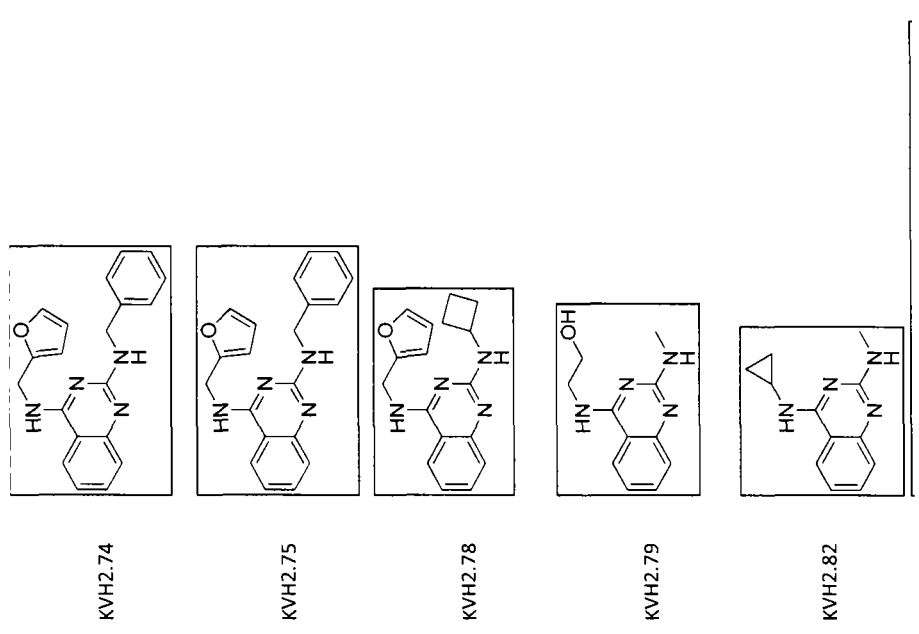
FIG 6.M, TABLE 1.M

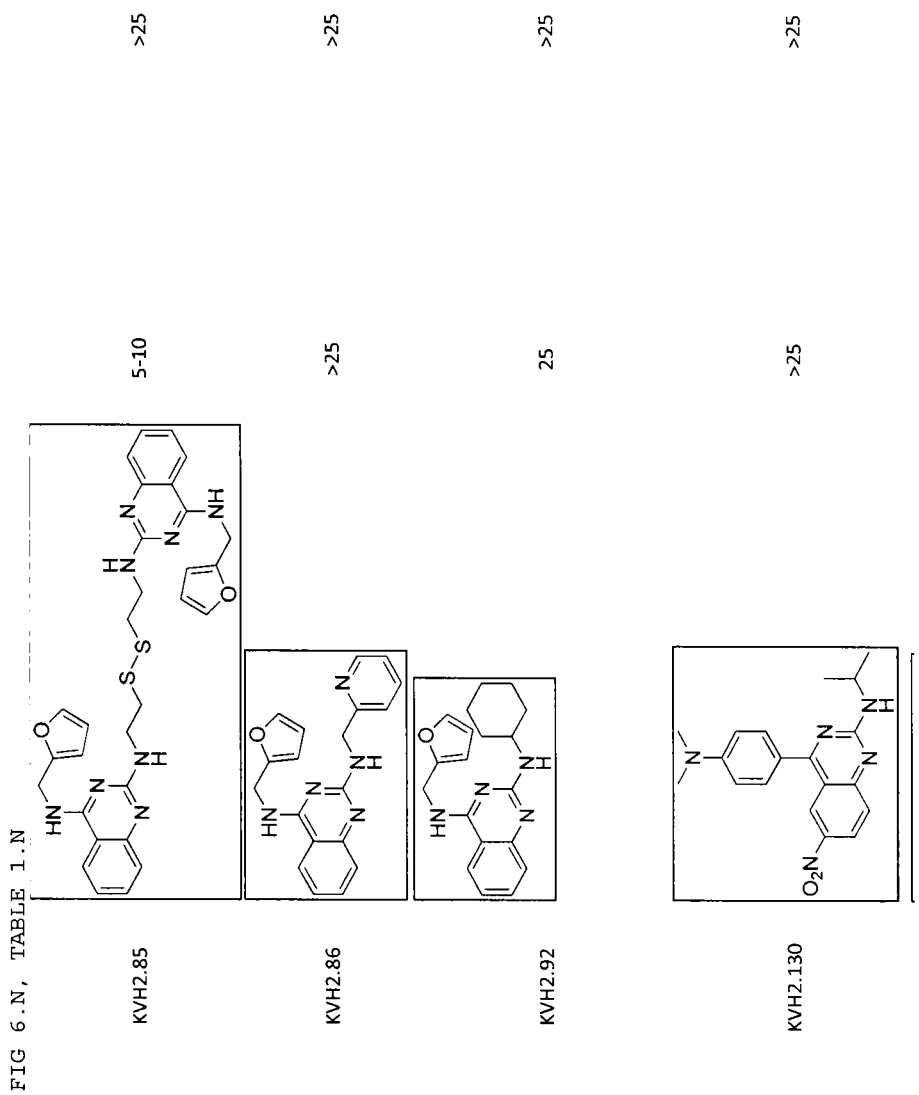
FIG 6.N, TABLE 1.N

FIG 6.0, TABLE 1.0
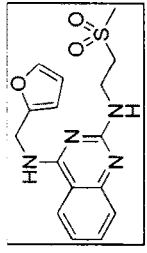
KVH2.135
50-100
>25
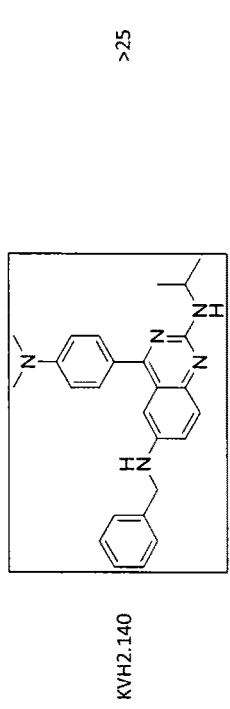
KVH2.140
>25
>25
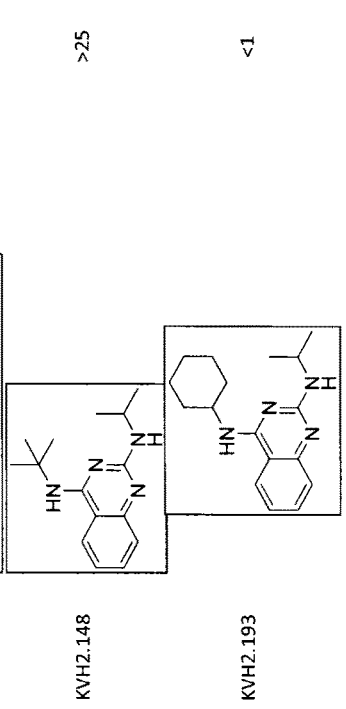
KVH2.148
>25
>25
KVH2.193
<1
ND
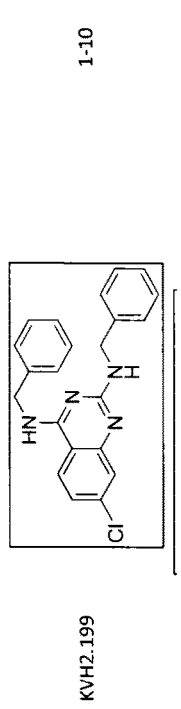
KVH2.199
1-10
>25

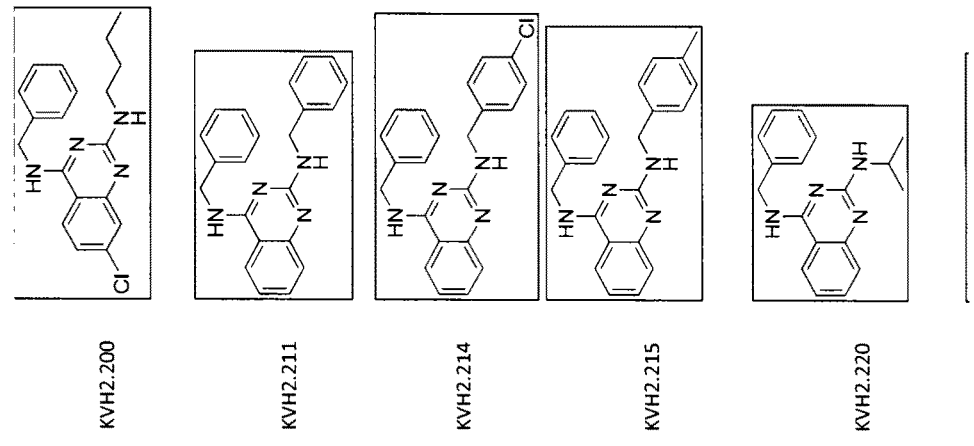
FIG 6.P, TABLE 1.P

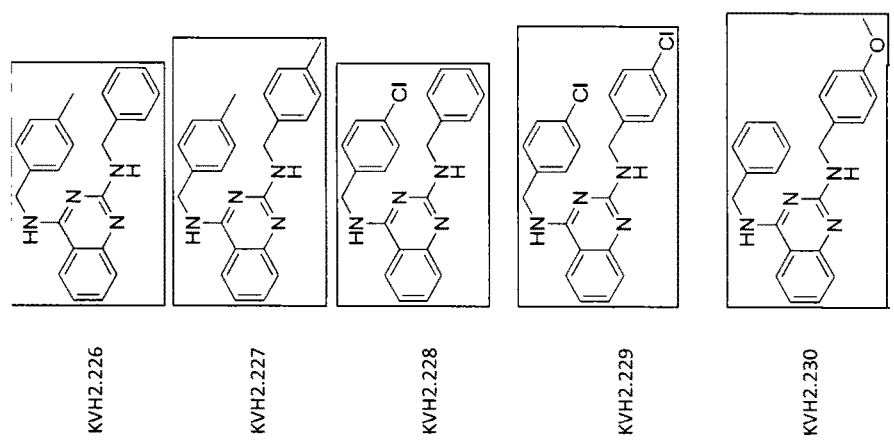
FIG 6.Q, TABLE 1.Q

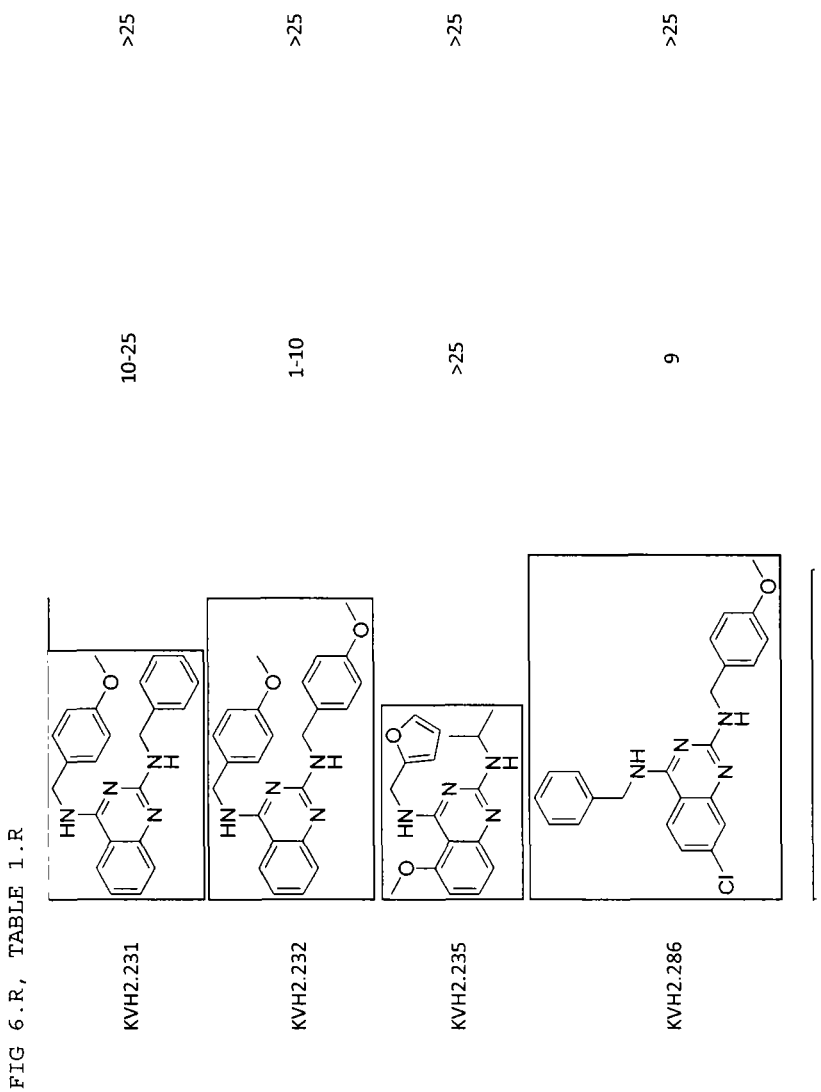
FIG 6.R, TABLE 1.R

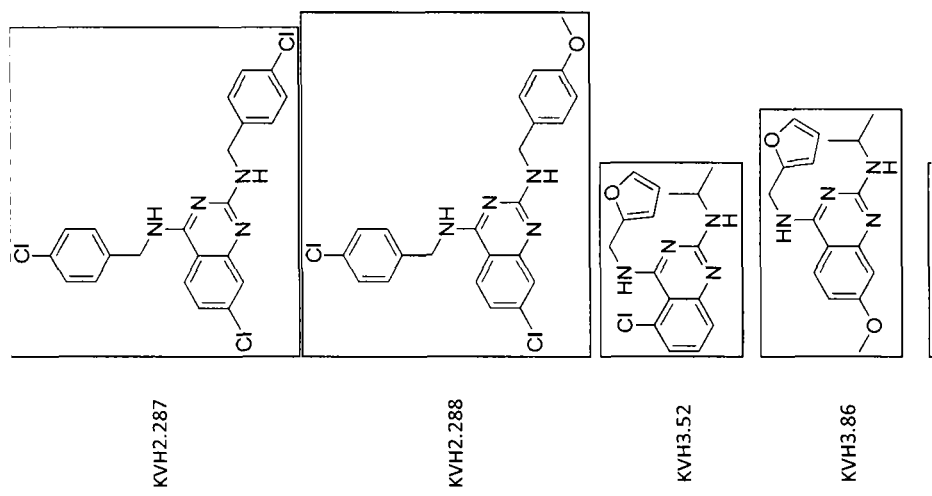
FIG 6.S, TABLE 1.S

FIG 6.T, TABLE 1.T
| | | | | |
|---|---|---|---|---|
| KVH2.93 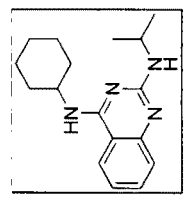 | >25 | <1 | <1 | |
| KVH3.96 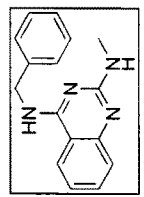 | 5 | ND | <1 | |
| KVH3.152 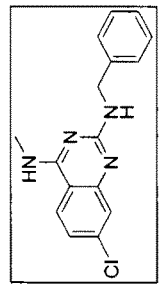 | 10 | ND | | |
| KVH3.157 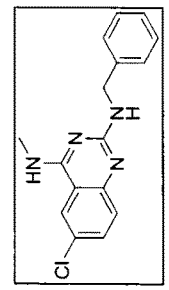 | 0.5 | ND | | |

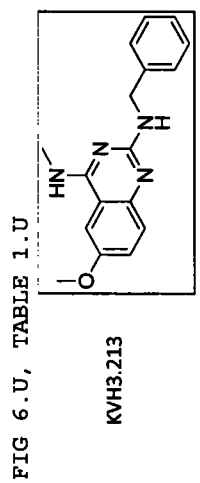
FIG 6.U, TABLE 1.U
KVH3.213
ND

COMPOSITIONS, METHODS OF USE, AND METHODS OF TREATMENT

CROSS-REFERENCE TO RELATED APPLICATIONS

This application is a divisional of and claims priority U.S. non-provisional patent application entitled "Compositions, Methods of Use, and Methods of Treatment", having Ser. No. 13/848,846, filed Mar. 22, 2013, which claims priority to U.S. provisional application entitled "2,4-Diaminoquinazolines as Anti-Bacterials" having Ser. No. 61/614,849, filed on Mar. 23, 2012, each of which is entirely incorporated herein by reference.

BACKGROUND

Despite the notable success of antibiotics in the past 70 years, bacterial diseases remain the second-leading cause of mortality worldwide. Bacteria cause 17 million deaths globally, particularly in children and the elderly. In the United States, there are almost 2 million hospital acquired infections each year, resulting in approximately 100,000 deaths. Perhaps the most significant public health concern in the context of bacterial infectious disease is the continued and rapid emergence of drug resistant bacteria during antibiotic treatment. Many bacteria are now unresponsive to conventional therapeutics, whilst they still continue to cause community and hospital acquired infections worldwide, leading to life-threatening and lethal diseases. As such, there is an undeniable and desperate need to develop new antibacterial therapeutics to fight the infections caused by these virtually untreatable pathogens,

SUMMARY

The present disclosure provides compositions including a 2,4-diaminoquinazoline compound (e.g., $N^2,N^4$-disubstituted 2,4-diaminoquinazoline compound), pharmaceutical compositions including a 2,4-diaminoquinazoline compound, methods of treatment of a condition (e.g., bacterial infection) or related disease, methods of treatment using compositions or pharmaceutical compositions, and the like. An embodiment of the present disclosure can be used to treat bacteria and resistant strains of bacteria (e.g., methicillin-resistant *Staphylococcus aureus* (MRSA)). In addition, embodiments of the present disclosure are broad spectrum antibiotics.

In an embodiment, a composition, among others, includes: a 2,4-diaminoquinazoline compound. In an embodiment, the 2,4-diaminoquinazoline compound is represented by any one of the structures described by structure A:

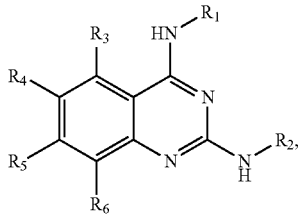

Structure A wherein R1 is selected from an alkyl group, a benzyl group, an aryl group, a heteroaryl group, or a cyclic or heterocyclic group, wherein any one of these optionally includes an alkyl group connecting the group to N, where each is independently substituted or unsubstituted; wherein R2 is selected from an alkyl group, a benzyl group, an aryl group, a heteroaryl group, or a cyclic or heterocyclic group, wherein any one of these optionally includes an alkyl group connecting the group to N, where each is substituted or unsubstituted; and each of R3, R4, R5, and R6 are independently selected from: H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkyny, where each ring containing group is optionally connected to the benzene ring of the scaffold using an alkyl group.

In an embodiment, a pharmaceutical composition, among others, includes: a therapeutically effective amount of a 2,4-diaminoquinazoline compound, or a pharmaceutically acceptable salt of the 2,4-diaminoquinazoline compound, and a pharmaceutically acceptable carrier, to treat a condition.

In an embodiment, a method of treating a condition, among others, includes: delivering to a subject in need thereof, a pharmaceutical composition, wherein the pharmaceutical composition includes a therapeutically effective amount of a 2,4-diaminoquinazoline compound, or a pharmaceutically acceptable salt of the 2,4-diaminoquinazoline compound, and a pharmaceutically acceptable carrier, to treat the condition.

In an embodiment, a method of regulating or preventing biofilm formation, among others, includes: contacting an effective amount of a 2,4-diaminoquinazoline compound to a surface, wherein the amount is effective to regulate biofilm formation on the surface.

Other structures, compositions, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 6A-6U show Tables 1A-1U, where embodiments of the compounds are shown and the concentrations of each compound needed to kill the listed bacteria are shown.

DISCUSSION

Figure 1:
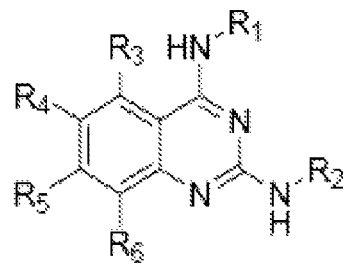
FIG. 1 illustrates an embodiment of a 2,4-diaminoquinazoline compound.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of organic chemistry, biochemistry, microbiology, molecular biology, pharmacology, medicine, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions:

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "substituted" refers to any one or more hydrogens on the designated atom that can be replaced with a selection from the indicated group, provided that the designated atom's normal valence is not exceeded, and that the substitution results in a stable compound. In an embodiment, the term "substituted" means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, indazolyl, quinolyl, isoquinolyl, quinoxalyl, and quinazolinyl. Preferred examples are furanyl, indazolyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—S(O)CH$_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —S(O$_2$)—R, wherein R may be, but is not limited to, alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—S(O$_2$)CH$_3$) and the like.

The term "phosphite" as used herein, alone or in combination, refers to a phosphorus atom covalently linked to three carbon atoms, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998).

The Use of Esters as Prodrugs for Oral Delivery of β-Lactam antibiotics, Pharm. Biotech. 11, 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a composition of the present disclosure into a host. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition, a disease or a disorder with a composition to affect the condition, disease or disorder by improving or altering it. The improvement or alteration may include an improvement in symptoms or an alteration in the physiologic pathways associated with the condition, disease, or disorder. "Treatment," as used herein, covers one or more treatments of a tumor or a disease in a host (e.g., a mammal, typically a human or non-human animal of veterinary interest), and includes: (a) reducing the risk of occurrence of the disease in a subject determined to be predisposed to the condition or disease but not yet diagnosed with it (b) impeding the development of the condition or disease, and/or (c) relieving the condition disease, e.g., causing regression of the condition or disease and/or relieving one or more disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition, a disease, or a symptom thereof and/or may be therapeutic in terms of a partial or complete cure for a condition, a disease, and/or adverse effect attributable to the disease.

As used herein, the term "host," "subject," or "patient," includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The phrase "bacterial infection" can refer to a bacteria colonizing the blood, a tissue and/or an organ of a subject, where the colonization causes harm to the subject. The harm can be caused directly by the bacteria and/or by toxins produced by the bacteria. Reference to bacterial infection includes also includes bacterial disease. Antibiotic agents, such as those described herein, can kill bacteria, prevent bacterial growth, and/or assist the subjects ability to kill or prevent bacteria growth.

Bacteria that cause bacterial infection are called pathogenic bacteria. The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium*, and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Pepto-* coccus, *Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae).

Biofilms are biological films that develop and persist at interfaces in aqueous environments, especially along the inner walls of conduit material in industrial facilities, in household plumbing systems, on medical implants, or as foci of chronic infections. These biological films are composed of microorganisms embedded in an organic gelatinous structure composed of one or more matrix polymers that are secreted by the resident microorganisms. Biofilms can develop into macroscopic structures several millimeters or centimeters in thickness and can cover large surface areas. These biological formations can play a role in restricting or entirely blocking flow in plumbing systems and often decrease the lifespan or longevity of materials through corrosive action mediated by the embedded bacteria. Biofilms are also capable of trapping nutrients and particulates that can contribute to their enhanced development and stability. Biofilms can also prevent penetration of antimicrobial agents and therefore, make bacteria within biofilms drug resistant, which leads to persistent infection.

Discussion:

The present disclosure provides compositions including a 2,4-diaminoquinazoline compound (e.g., $N^2,N^4$-disubstituted 2,4-diaminoquinazoline compound), pharmaceutical compositions including a 2,4-diaminoquinazoline compound, methods of treatment of a condition (e.g., bacterial infection) or related disease, methods of treatment using compositions or pharmaceutical compositions, and methods of regulating biofilm growth, and the like. An embodiment of the present disclosure can be used to treat bacteria and resistant strains of bacteria (e.g., methicillin-resistant *Staphylococcus aureus* (MRSA)). In addition, embodiments of the present disclosure are broad spectrum antibiotics. Additional details are described in the Examples.

An embodiment of the present disclosure includes a composition and pharmaceutical composition including a 2,4-diaminoquinazoline compound. In an embodiment, the pharmaceutical composition and the method of treatment (e.g., of an infection such as one directly or indirectly caused by a bacterial infection (e.g., gram-positive and/or gram-negative bacteria)) includes a therapeutically effective amount of the 2,4-diaminoquinazoline compound, or a pharmaceutically acceptable salt of the 2,4-diaminoquinazoline compound, and a pharmaceutically acceptable carrier, to treat a condition (e.g., bacterial infection). In particular, 2,4-diaminoquinazoline compound can be used as a broad spectrum antibiotic. Embodiments of the present disclosure have been shown to treat and cure animals infected with bacteria (e.g., MSRA).

In an embodiment the bacterial infections can be caused by one or more types of bacteria, in particular, drug or multidrug resistant bacteria. In an embodiment, the bacterial infection can be caused by gram-positive and/or gram negative bacteria. In an embodiment, the bacteria can include, but is not limited to, *Staphylococcus aureus* (e.g., MRSA), *Streptococcus pyogenes, Streptococcus pneumonia, Enterococcus faecalis, Enterococcus faecium, Pseudomonas aeruginosa, Clostridium difficile, Escherichia coli, Salmonella, Acinetobacter baumannii, Mycobacterium tuberculosis,* or a combination thereof.

In an embodiment, the 2,4-diaminoquinazoline compound can be used to regulate (e.g., inhibiting, attenuating, etc) biofilms caused by bacteria. In an embodiment, the methods are suitable for preventing bacteria from accruing. In an embodiment, the biofilm can be treated with the 2,4-diaminoquinazoline compound for a period of time (e.g., 24 hours) and has been shown to kill bacteria of the biofilm.

Compositions of the present disclosure can be used to regulate bacteria growing (e.g., the penetrate the aggregate matrix of a biofilm and exert bactericidal effects on the cells contained within) on hard, rigid structures or surfaces such as drain pipes, glazed ceramic, porcelain, glass, metal, wood, chrome, plastic, vinyl, and formica or soft flexible structures or surfaces such as shower curtains, upholstery, laundry, sponges, mops, wipes, and carpeting, by contacting an effective amount of the compound to a structure or surface of a structure to inhibit additional bacteria growth and kill bacteria that are present, for example in a biofilm. In addition, methods of the present disclosure can be used to treat both woven and non-woven and porous and non-porous surfaces would be suitable. In an embodiment, the method includes administering (e.g., in the water source) or contacting an effective amount of the compounds to large-scale sanitation applications, systems, or structures, such as food production machinery (e.g., raw meat, fish, pork, and poultry processing equipment, as well as fruit and vegetable processing equipment), sanitation equipment, processing areas, and conduits that carry raw materials or finished products. In an embodiment, the method can use the composition to inhibit growth in a mouthwash, in toothpaste, for the treatment of dental carriers, acne treatment, cleaning and disinfecting contact lenses, and medically implanted devices that are permanent such as an artificial heart valve or hip joint, and those that are not permanent such as indwelling catheters, pacemakers, surgical pins, and the like.

In an embodiment, methods of the present disclosure can use (e.g., administer to the host and/or apply to the devices) the composition to inhibit growth in medically implanted devices that are permanent devices (e.g., an artificial heart valve or hip joint), and those that are not permanent devices (e.g., indwelling catheters, pacemakers, surgical pins, and the like) to regulate bacteria as it relates to the medically implanted devices.

The term "effective amount" in regard to bacterial growth or biofilms on non-living structures can include an amount of the compound to achieve regulation of the bacteria. The effective amount is determined, at least in part, upon the compound used, the bacteria present, the structure, system, or host, and the desired level of regulation. In an embodiment, regulation includes slowing, attenuating, inhibiting new bacteria, killing bacteria that are present, inhibiting the growth of a biofilm, and the like. In an embodiment, regulation includes slowing the formation of bacteria in a biofilm.

In an embodiment, the 2,4-diaminoquinazoline compound can include $N^2,N^4$-disubstituted 2,4-diaminoquinazoline compound, pharmaceutically acceptable salt thereof, or a prodrug thereof. In an embodiment, the $N^2,N^4$-disubstituted 2,4-diaminoquinazoline compound can have the following structure (Structure A):

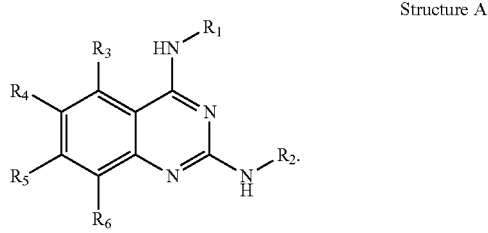

Structure A

In an embodiment, R1 can be selected from an alkyl group (e.g., linear or branched, C1 to C5 hydrocarbons such as methyl, ethyl, propyl, butyl, and the like), a benzyl group, an aryl group, a heteroaryl group, or a cyclic or hetero (e.g., O, N) cyclic group (e.g., C1 to C7 cyclic hydrocarbons), where any one of these rings can include an alkyl group connecting the group to the N, where each can be substituted or unsubstituted. In an embodiment, the alkyl group can be a butyl group, linear or branched, substituted or unsubstituted.

In an embodiment, R2 can be selected from an alkyl group (e.g., linear or branched, C1 to C5 hydrocarbons such as methyl, ethyl, propyl, butyl, and the like), a benzyl group, an aryl group, a heteroaryl group, or a cyclic or hetero (e.g., O, N) cyclic group (e.g., C1 to C7 cyclic hydrocarbons), where any one of these rings can include an alkyl group connecting the group to the N, where each can be substituted or unsubstituted. In an embodiment, R2 can be a benzyl group, substituted or unsubstituted. In an embodiment, R1 is a butyl group, linear or branched, substituted or unsubstituted, and R2 can be a benzyl group, substituted or unsubstituted.

In an embodiment, each of R3, R4, R5, and R6 can be independently selected from H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkyny, where each ring containing group can be connected to the benzene ring of the scaffold using an alkyl group (e.g., aryl-alkyl-benzene ring of scaffold).

Figure 3:
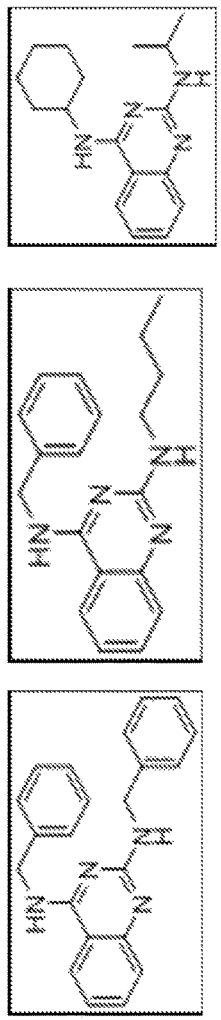
FIG. 3 illustrates embodiments of specific compounds of the 2,4-diaminoquinazoline compound. In addition, FIG. 3 lists concentrations of the compound that kill the listed bacteria.
Figure 3:
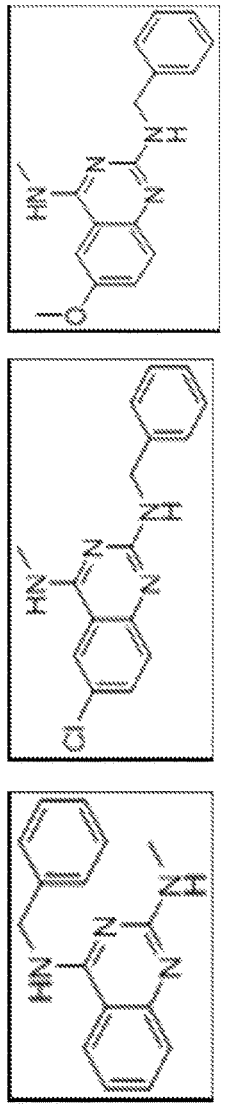

In an embodiment, R1 is a butyl group, linear or branched, substituted or unsubstituted, and R2 can be a benzyl group, substituted or unsubstituted. In an embodiment, the 2,4-diaminoquinazoline compound can include the structures as shown in FIG. 3 and FIGS. 6A to 6U, which show Tables 1A to 1U.

It should be noted that the therapeutically effective amount to result in uptake of the 2,4-diaminoquinazoline compound into the host will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Figure 2:
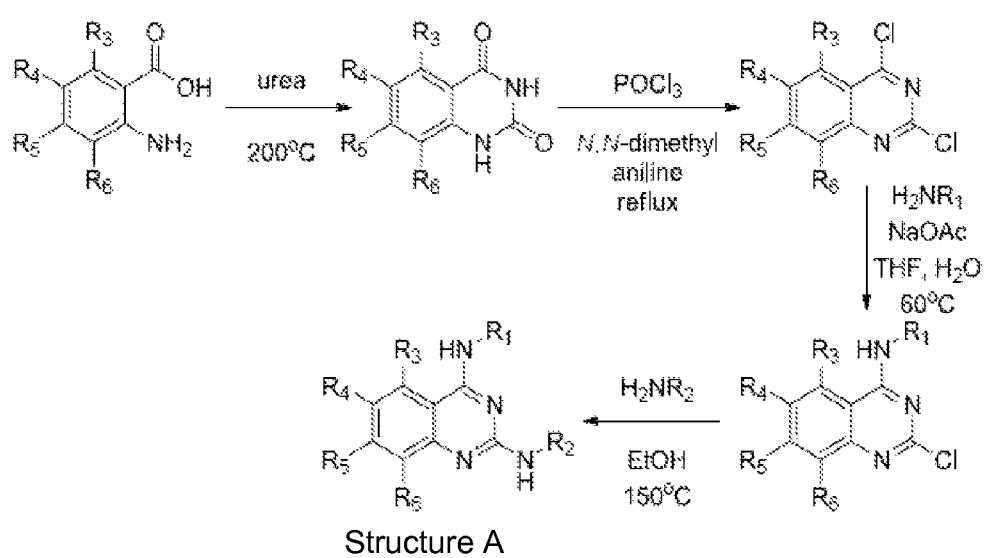
FIG. 2 illustrates an embodiment of a method of making a 2,4-diaminoquinazoline compound.

FIG. 2 illustrates an embodiment of a method of making Structure A. Exemplary description of the method is described below. Appropriate modification of the reagents can be made to accommodate the various R groups.

General Procedure A: Cyclization of Anthranilic Acids to the Corresponding Quinazoline-2,4-diones: 1 equivalent of anthranilic acid and 3.5 equivalents of urea were mortar and pestled to a powder and heated to about 200° C. in a round bottom open to the atmosphere. After two hours, the mixture was cooled, triturated with water, and filtered to give the product as crude. No further purification was performed.

General Procedure B: Chlorination of Quinazoline-2,4-diones to the Corresponding 2,4-Dichloroquinazolines: 1 equivalent of quinazoline-2,4-dione and 1 equivalent of N,N-dimethylaniline were mixed in 12 equivalents of phosphorous oxychloride and the mixture refluxed under an argon atmosphere until starting material was no longer present by TLC (about 3-16 hours). The mixture was then cooled and added to ice in the amount of ten times the reaction volume. The solution was filtered to give crude product.

General Procedure C: Amine Substitution of 2,4-Dichloroquinazolines to Yield 4-Amino-substituted 2-Chloroquinazolines: 1.1 equivalents of amine and sodium acetate were mixed with 1 equivalent of 2,4-dichloroquinazoline at 0.1 M concentration in a 3 to 1 mix of tetrahydrofuran and water and heated to about 65° C. When the reaction was observed to be finished by TLC, the solution was diluted with ethyl acetate, the layers were separated, and the organic phase washed three times with an equal amount of water and dried over $Na_2SO_4$. The crude was then purified by either method Ca or Cb:

Purification Method Ca: the compound was recrystallized with ethanol and water, filtered, and rinsed with cold ethanol to yield pure product.

Purification Method Cb: the crude was purified by flash chromatography using hexanes and ethyl acetate.

General Procedure D: Amine Substitution of 4-Amino-substituted-2-chloroquinazolines to Yield 2,4-Diamino-substituted Quinazolines: 1.5 equivalents of amine was mixed with 1 equivalent of 4-amino-substituted 2-chloroquinazoline at 0.2 M concentration in ethanol in a sealed tube and heated to 150° C. When the reaction was finished as observed by TLC, the compound was purified by either method Da or Db:

Purification Method Da: compound crystallized out of the cool solution, was filtered, and rinsed with cold ethanol to yield pure product.

Purification Method Db: solvent was evaporated and the crude mixture was purified by flash chromatography using dichloromethane and methanol.

Pharmaceutical Formulations and Routes of Administration

Embodiments of the present disclosure include a 2,4-diaminoquinazoline compound as identified herein and can be formulated with one or more pharmaceutically acceptable excipients, diluents, carriers and/or adjuvants. In addition, embodiments of the present disclosure include a 2,4-diaminoquinazoline compound formulated with one or more pharmaceutically acceptable auxiliary substances. In particular 2,4-diaminoquinazoline compound can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the 2,4-diaminoquinazoline compound can be administered to the host using any means capable of resulting in the desired effect. Thus, the 2,4-diaminoquinazoline compound can be incorporated into a variety of formulations for therapeutic administration. For example, the 2,4-diaminoquinazoline compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the 2,4-diaminoquinazoline compound may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the 2,4-diaminoquinazoline compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the 2,4-diaminoquinazoline compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the 2,4-diaminoquinazoline compound can be utilized in aerosol formulation to be administered via inhalation. Embodiments of the 2,4-diaminoquinazoline compound can be formulated into pressurized acceptable propellants such as dichlorodifluoromethane, propane, nitrogen and the like.

Furthermore, embodiments of the 2,4-diaminoquinazoline compound can be made into suppositories by mixing with a variety of bases such as emulsifying bases or water-soluble bases. Embodiments of the 2,4-diaminoquinazoline compound can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the 2,4-diaminoquinazoline compound in a composition as a solution in sterile water, normal saline or another pharmaceutically acceptable carrier.

Embodiments of the 2,4-diaminoquinazoline compound can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the 2,4-diaminoquinazoline compound can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the 2,4-diaminoquinazoline compound can be accomplished using any of a variety of refillable, pump systems. Pumps provide consistent, controlled release over time. In some embodiments, the 2,4-diaminoquinazoline compound can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the 2,4-diaminoquinazoline compound) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350, 155; 5,443,450; 5,814,019; 5,976,109; 6,017,328; 6,171, 276; 6,241,704; 6,464,687; 6,475,180; and 6,512,954. A further exemplary device that can be adapted for the present disclosure is the Synchromed infusion pump (Medtronic).

Suitable excipient vehicles for the 2,4-diaminoquinazoline compound are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the 2,4-diaminoquinazoline compound adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the 2,4-diaminoquinazoline compound may be administered using intravenous infusion, an implantable osmotic pump, a transdermal patch, liposomes, or other modes of administration. In one embodiment, a pump may be used (Sefton (1987). *CRC Crit. Ref Biomed. Eng.* 14:201; Buchwald et al. (1980). *Surgery* 88:507; Saudek et al. (1989). *N Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the 2,4-diaminoquinazoline compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the 2,4-diaminoquinazoline compound can be administered to a host in one or more doses. Those of skill will readily appreciate that dose levels can vary as a function of the specific the 2,4-diaminoquinazoline compound administered, the severity of the symptoms and the susceptibility of the subject to side effects. Preferred dosages for a given compound are readily determinable by those of skill in the art by a variety of means.

In an embodiment, multiple doses of the 2,4-diaminoquinazoline compound are administered. The frequency of administration of the 2,4-diaminoquinazoline compound can vary depending on any of a variety of factors, e.g., severity of the symptoms, and the like. For example, in an embodiment, the 2,4-diaminoquinazoline compound can be administered once per month, twice per month, three times per month, every other week (qow), once per week (qw), twice per week (biw), three times per week (tiw), four times per week, five times per week, six times per week, every other day (qod), daily (qd), twice a day (qid), three times a day (tid), or four times a day. As discussed above, in an embodiment, the 2,4-diaminoquinazoline compound is administered 1 to 4 times a day over a 1 to 10 day time period.

The duration of administration of the 2,4-diaminoquinazoline compound analogue, e.g., the period of time over which the 2,4-diaminoquinazoline compound is administered, can vary, depending on any of a variety of factors, e.g., patient response, etc. For example, the 2,4-diaminoquinazoline compound in combination or separately, can be administered over a period of time of about one day to one week, about one day to two weeks.

Routes of Administration

Embodiments of the present disclosure provide methods and compositions for the administration of the active agent (e.g., the 2,4-diaminoquinazoline compound) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the 2,4-diaminoquinazoline compound) can be administered in a single dose or in multiple doses.

Embodiments of the 2,4-diaminoquinazoline compound can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the 2,4-diaminoquinazoline compound. Where systemic delivery is desired, administration typically involves invasive or systemically absorbed topical or mucosal administration of pharmaceutical preparations.

In an embodiment, the 2,4-diaminoquinazoline compound can also be delivered to the subject by enteral administration. Enteral routes of administration include, but are not limited to, oral and rectal (e.g., using a suppository) delivery.

Methods of administration of the 2,4-diaminoquinazoline compound through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

FIG. 3 and FIGS. 6A to 6U (Tables 1A to 1U) illustrate embodiments of specific compounds of the 2,4-diaminoquinazoline compound. In addition, FIG. 3 and FIGS. 6A to 6U list concentrations of the compound that kill the listed bacteria. These data were generated by growing either Methicillin Resistant *Staphylococcus aureus* (MRSA) or *Acinetobacter baumannii* (as listed) in a range of concentrations of the named 2,4-diaminoquinazoline compounds. After overnight incubation, cultures were inspected for bacterial growth. The minimum inhibitory concentration (MIC) was determined as the lowest concentration able to completely inhibit bacterial growth.

Figure 4:
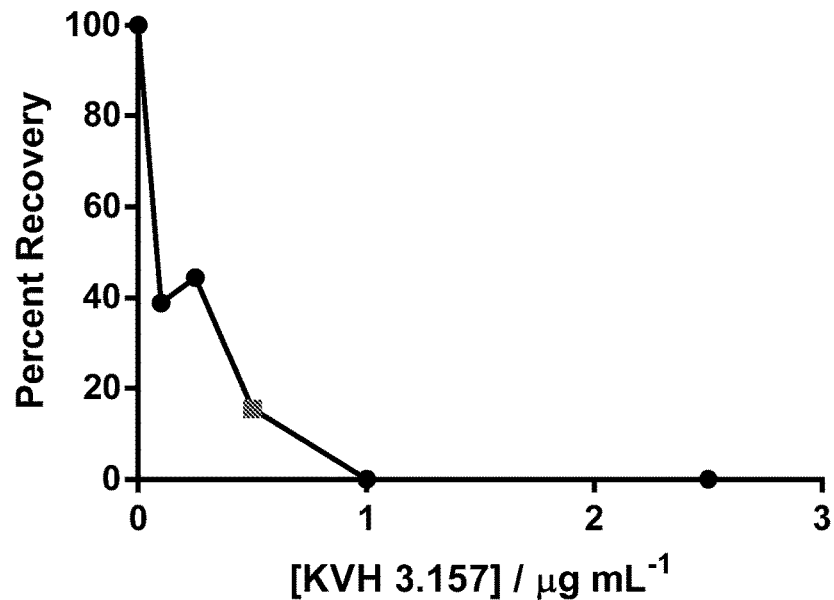
FIG. 4 illustrates a graph showing the effect of an embodiment of the compound on a biofilm.

*Acinetobacter baumannii* biofilms were allowed to establish in microtitre plates overnight, before being exposed to increasing concentrations on KVH 3.157. After 24 h incubation, the percentage of cells recovered from exposed biofilms compared to untreated controls, were determined (See FIG. 4). The lighter colored square refers to the minimum concentration of this compound that inhibits bacterial growth.

Figure 5:
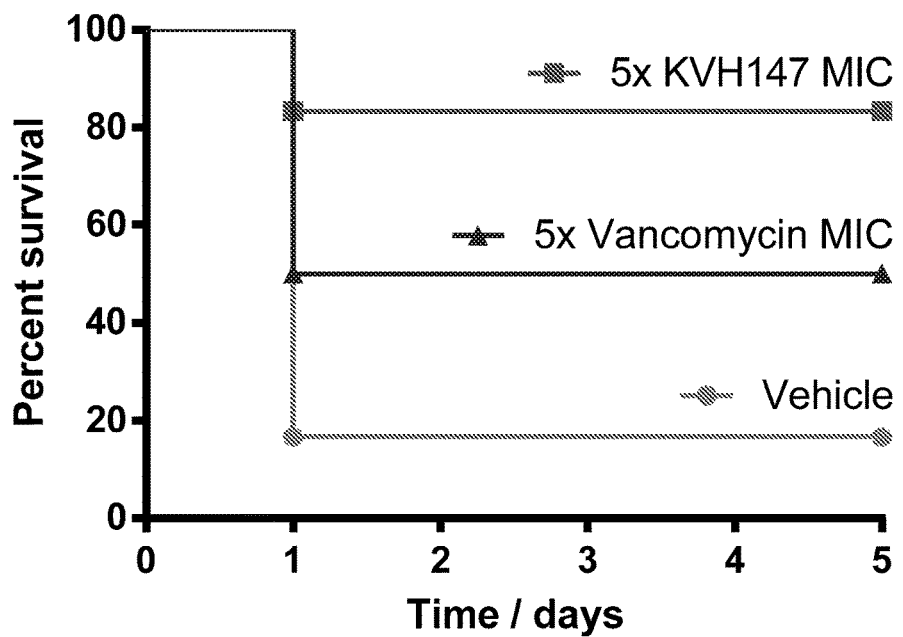
FIG. 5 illustrates a graph showing the effect of an embodiment of the compound on treating a bacterial infection in mice.

Three groups of 6 mice were infected by intraperitoneal injection with a lethal dose of MRSA (See FIG. 5). 1 h following this, animal were injected into the tail vein with either Vehicle alone (negative control), 5×MIC of vancomycin (positive control) or 5×MIC of KVH1.147. Animals were monitored for survival over the course of 5 days.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A method of treating a condition comprising: delivering to a subject in need thereof, a pharmaceutical composition, wherein the pharmaceutical composition includes a therapeutically effective amount of a 2,4-diaminoquinazoline compound, or a pharmaceutically acceptable salt of the 2,4-diaminoquinazoline compound, and a pharmaceutically acceptable carrier, to treat the condition, wherein the 2,4-diaminoquinazoline compound is represented by any one of the structures described by structure A:

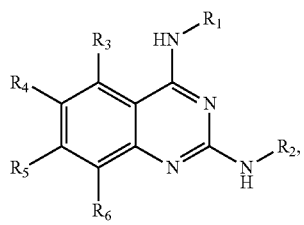

Structure A wherein the R1 group is a linear or branched, substituted or unsubstituted, butyl group, and wherein the R2 group is a substituted or unsubstituted benzyl group; and each of R3, R4, R5, and R6 are independently selected from: H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkyny;

wherein the condition is a bacterial infection.

2. The method of claim 1, wherein the bacterial infection is caused by *Acinetobacter baumannii*.

3. The method of claim 1, wherein the bacterial infection is caused by methicillin-resistant *Staphylococcus aureus*.

4. A method of regulating or preventing bacterial-based biofilm formation, comprising:
contacting an effective amount of a 2,4-diaminoquinazoline compound to a surface, wherein the amount is effective to regulate biofilm formation on the surface, wherein the 2,4-diaminoquinazoline compound is represented by any one of the structures described by structure A:

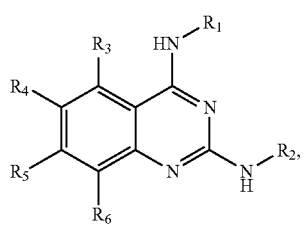

Structure A wherein the R1 group is a linear or branched, substituted or unsubstituted, butyl group, and wherein the R2 group is a substituted or unsubstituted benzyl group; and each of R3, R4, R5, and R6 are independently selected from: H, a halogen, a substituted or unsubstituted alkyl, a substituted or unsubstituted aryl, a substituted or unsubstituted cycloalkyl, a substituted or unsubstituted cycloalkenyl, a substituted or unsubstituted heteroaryl, a substituted or unsubstituted biaryl, a substituted or unsubstituted fused aryl, a substituted or unsubstituted alkenyl, or a substituted or unsubstituted alkyny.

5. The method of claim 4, wherein the bacterial-based biofilm formation is caused by methicillin-resistant *Staphylococcus aureus*.

6. The method of claim 4, wherein the bacteria include Gram-positive and Gram-negative bacteria.

7. The method of claim 4, wherein the bacterial infection is caused by methicillin-resistant *Staphylococcus aureus*.

8. The method of claim 4, wherein the bacterial-based biofilm formation is caused by *Acinetobacter baumannii*.

9. A method of treating a bacterial infection comprising: delivering to a subject in need thereof, a pharmaceutical composition, wherein the pharmaceutical composition includes a therapeutically effective amount of a 2,4-diaminoquinazoline compound, or a pharmaceutically acceptable salt of the 2,4-diaminoquinazoline compound, and a pharmaceutically acceptable carrier, to treat the condition, wherein the 2,4-diaminoquinazoline compound is represented by any one of the structures described by the following:

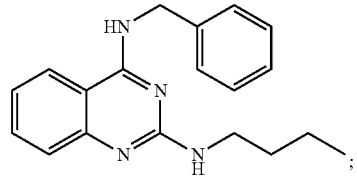

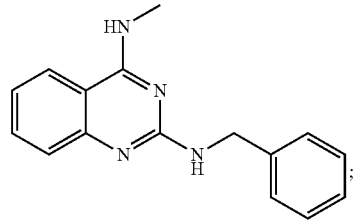

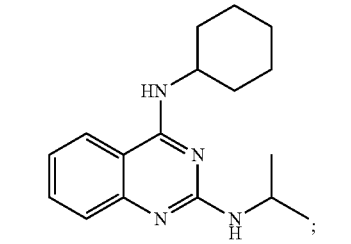

; and

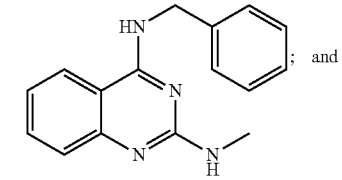

-continued

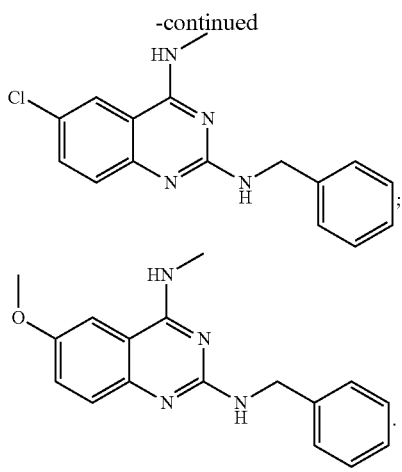

10. The method of claim 9, wherein the bacteria include Gram-positive and Gram-negative bacteria.

11. The method of claim 9, wherein the bacterial infection is caused by methicillin-resistant *Staphylococcus aureus*.

12. The method of claim 9, wherein the bacterial infection is caused by *Acinetobacter baumannii*.

13. A method of regulating or preventing bacterial-based biofilm formation, comprising:
    contacting an effective amount of a 2,4-diaminoquinazoline compound to a surface, wherein the amount is effective to regulate biofilm formation on the surface, wherein the 2,4-diaminoquinazoline compound is represented by any one of the structures described by the following:

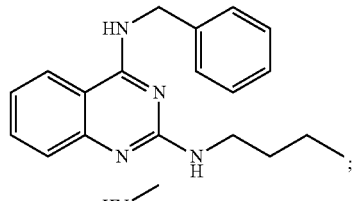

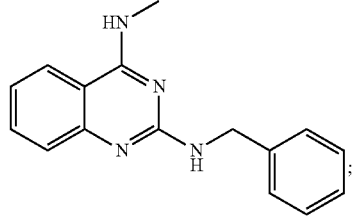

-continued

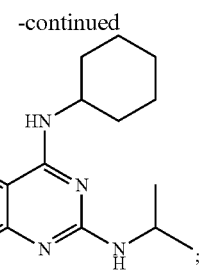

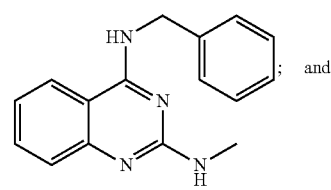

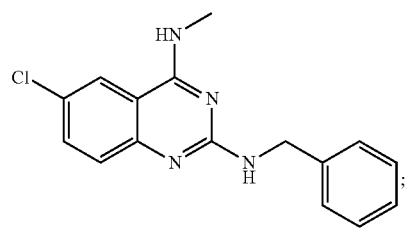

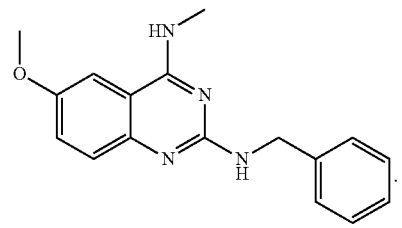

14. The method of claim 13, wherein the bacterial-based biofilm formation is caused by methicillin-resistant *Staphylococcus aureus*.

15. The method of claim 13, wherein the bacterial-based biofilm formation is caused by *Acinetobacter baumannii*.

* * * * *